United States Patent [19]

Ager et al.

[11] 4,329,293

[45] May 11, 1982

[54] TRIALKYLAMINE/SULFUR DIOXIDE CATALYZED SULFENYLATION OF CARBAMATES

[75] Inventors: John W. Ager; Maurice J. C. Harding, both of Princeton; Charles E. Hatch, III, Pennington, all of N.J.

[73] Assignee: FMC Corporation, Philadelphia, Pa.

[21] Appl. No.: 202,526

[22] Filed: Oct. 31, 1980

[51] Int. Cl.³ ............... C07D 307/86; C07C 145/04; C07C 195/04

[52] U.S. Cl. ........................... 549/470; 544/3; 544/59; 544/153; 544/159; 544/164; 544/383; 546/195; 546/238; 548/356; 549/19; 549/28; 260/239 R; 260/239 BC; 260/239 BF; 260/465 D; 260/465.4; 260/968; 560/16; 560/17; 560/148; 564/225; 548/517; 548/525; 548/542; 549/371; 549/424; 549/438; 549/449; 549/452; 549/480

[58] Field of Search ............... 260/346.73; 560/16, 560/17, 148; 564/255

[56] References Cited

U.S. PATENT DOCUMENTS

| | | | |
|---|---|---|---|
| 3,847,951 | 11/1974 | Kohn et al. | 260/346.2 |
| 3,980,673 | 9/1976 | Siegle et al. | 260/346.2 |
| 3,997,549 | 12/1976 | Fukuto et al. | 260/306.6 |
| 4,006,231 | 2/1977 | Black et al. | 424/248.5 |
| 4,108,991 | 8/1978 | Fukuto et al. | 424/248.5 |

*Primary Examiner*—Henry R. Jiles
*Assistant Examiner*—Bernard Dentz
*Attorney, Agent, or Firm*—Robert L. Andersen; H. Robinson Ertelt

[57] ABSTRACT

An improved process is disclosed for sulfenylating carbamates in the presence of a solvent and acid acceptor, in which the reaction between a carbamate and a sulfenyl halide is conducted in the presence of a catalytic amount of a complex of a lower alkylamine and sulfur dioxide. Several methods for preparing and utilizing the complex in the reaction are disclosed and exemplified.

14 Claims, No Drawings

TRIALKYLAMINE/SULFUR DIOXIDE CATALYZED SULFENYLATION OF CARBAMATES

The present invention relates to a process for sulfenylating carbamates with a sulfenyl halide in the presence of a solvent and a hydrogen halide acceptor. More particularly the invention relates to a method for decreasing reaction times and improving product yields and purity by reacting a carbamate with a sulfenyl halide in the presence of a catalytic amount of a complex of sulfur dioxide and a trialkylamine.

The reaction of an aminosulfenyl halide with a carbamate in the presence of a solvent and an acid acceptor is known. For example U.S. Pat. No. 4,006,231 describes the preparation of aminothio derivatives of carbofuran, the common name for 2,3-dihydro-2,2-dimethyl-7-benzofuranyl methylcarbamate, by reacting together carbofuran and an aminosulfenyl halide in pyridine, the pyridine serving as solvent and acid acceptor for the reaction, the reaction taking place over a period of about 18 hours. Similarly, U.S. Pat. No. 4,108,991 discloses a comparable reaction in which aldicarb, the common name for 2-methyl-2-methylthiopropanal O-(methylcarbamoyl)oxime, is reacted with an aminosulfenyl halide in the presence of pyridine. U.S. Pat. No. 3,847,951 discloses that arylthio or alkylthio carbamates may be prepared by the reaction of an alkylsulfenyl or arylsulfenyl halide and carbofuran in the presence of an amine base, such as triethylamine, pyridine, or quinuclidine, and an aprotic organic solvent such as dimethylformamide.

U.S. Pat. No. 3,980,673 teaches, for the reaction of an arylsulfenyl chloride with carbofuran, that one may employ as solvents an ether such as diethyl ether, dioxane, or tetrahydrofuran, a hydrocarbon such as benzene, or chlorinated hydrocarbons such as chloroform or chlorobenzene. This patent also discloses, for aryl sulfenylation, that a tertiary organic base such as triethylamine is the preferred acid-binding agent. U.S. Pat. No. 3,997,549 teaches reacting the reaction product of sulfuryl chloride and 4-t-butylbenzenethiol in pyridine with carbofuran to produce 2,3-dihydro-2,2-dimethyl-7-benzofuranyl (4-t-butylphenylthio)(methyl)carbamate.

Unless otherwise specified in the specification and claims which follow, the term "lower" as applied to an aliphatic group such as alkyl means a group having 1 to 6, preferably 1 to 4 carbon atoms, and the terms "halo" or "halogen" include bromine, chlorine or fluorine. The symbol $\phi$ is used in the tables to designate a phenyl group.

The present invention provides an improved process for sulfenylating a carbamate in the presence of a solvent and an acid acceptor to produce a corresponding sulfenylated derivative in which the free hydrogen has been replaced by a sulfenyl group. In the improved process substantially improved yields and purity are obtained together with dramatically decreased reaction times. The invention resides in conducting the reaction in the presence of a catalytic amount of a complex of sulfur dioxide and a trialkylamine.

The improved process is broadly applicable to reaction of N-alkyl carbamates of the general formula $R^1OOCR^2NH$, with a sulfenyl halide of the formula $R^3SX$ to produce a corresponding sulfenylated derivative of the general formula $R^1OOCR^2N-S-R^3$, in which the free hydrogen has been replaced with the $-SR^3$ group.

Such reactions are frequently slow, requiring many hours to complete, and frequently produce a sulfenylated product in low yields and of low purity. The general reaction is illustrated by equation A:

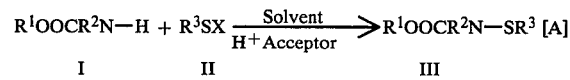

$$R^1OOCR^2N-H + R^3SX \xrightarrow[H^+ \text{Acceptor}]{\text{Solvent}} R^1OOCR^2N-SR^3 \quad [A]$$

I  II  III

In accordance with the present invention, reaction times, product yields and purity are substantially improved under similar conditions by conducting this reaction in the presence of a catalytic amount of a complex of sulfur dioxide ($SO_2$) and a trialkylamine (TA).

The complexes employed in this invention, sometimes referred to by the symbol $TA.SO_2$, generally contain substantially equimolar amounts of the trialkylamine and sulfur dioxide, but excess amounts of the amine or sulfur dioxide may be present in the reaction mixture if desired.

Suitable trialkylamines include compounds of the formula $R^4R^5R^6N$ in which $R^4$, $R^5$ and $R^6$ are alkyl groups of 1 to 4, preferably 1 to 2, carbon atoms. This includes amines such as triethylamine, trimethylamine and mixed trialkylamines. Triethylamine is the preferred amine for use in the reaction of a sulfenyl chloride with a heterocyclic alkylcarbamate such as carbofuran (2,3-dihydro-2,2-dimethyl-7-benzofuranyl methylcarbamate) and with an imino alkylcarbamate such as methomyl (methyl N-[[(methylamino)carbonyl]oxy]ethanimidothioate).

The complex of a trialkylamine and sulfur dioxide can be formed in several ways. It can be prepared separately by passing sulfur dioxide through a solution of the trialkylamine in an appropriate solvent, for example hexane. The resulting product may then be used without isolation of the complex in Reaction A. The sulfur dioxide and trialkylamine may also be added separately to a mixture of carbamate and sulfenyl halide and an appropriate solvent. Additionally, the sulfur dioxide may be formed in situ during preparation of the sulfenyl halide, by reacting an appropriate bis-disulfide with sulfuryl chloride, as illustrated in Reaction B

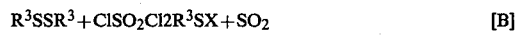

$$R^3SSR^3 + ClSO_2Cl2R^3SX + SO_2 \quad [B]$$

The resulting reaction mixture, containing $SO_2$ in solution, can then be combined with the trialkylamine to form the $TA.SO_2$ complex and the resulting mixture used without isolation in Reaction A. Also, the carbamate, acid acceptor and trialkylamine may be added to the product of Reaction B, so that the complex actually forms in situ during Reaction A. It is preferable to employ excess, preferably at least a 10 percent molar excess, of sulfenyl halide to carbamate in the reaction.

The amount of complex employed in the reaction of the sulfenyl halide with the carbamate can be varied, but must be at least an amount sufficient to catalyze the reaction, i.e. a catalytic amount. While the precise amounts needed may vary with the particular reactants, in general at least about 0.01 mole of catalyst complex per mole of carbamate should be present. About 0.03 up to about 0.3 mole per mole carbamate has been found to substantially improve reaction time, product yield, and product purity, but larger amounts, for example up to about 0.6 mole per mole of carbamate may be employed if desired.

Solvents suitable for the reaction of the sulfenyl halide with the carbamate include aromatic hydrocarbons of 6 to 10 carbon atoms such as benzene or toluene, halogenated aliphatic hydrocarbons of 1 to 4 carbon atoms such as methylene chloride, saturated aliphatic hydrocarbons of 5 to 10 carbon atoms, preferably 5 to 8 carbon atoms, such as petroleum ether, ligroin, heptane, hexane, or octane, ethers such as tetrahydrofuran, polar aprotic solvents such as dimethylformamide (DMF) or dimethylsulfoxide (DMSO), or aromatic nitrogen containing solvents such as pyridine. Most preferably, where a carbamate such as carbofuran is employed, saturated aliphatic hydrocarbons such as hexane or heptane are preferred because unreacted carbamate can be recovered by filtration due to its relatively low solubility in the solvent.

An acid or hydrogen halide acceptor is present to aid the reaction. Suitable acid acceptors are well known in this art. Preferred acid acceptors include pyridine or lower alkylamines such as triethylamine, but other tertiary or aromatic organic amines can be employed. The amount of acid acceptor employed in the reaction should at least be sufficient to take up or neutralize the amount of hydrogen halide formed during the course of the reaction. Thus from about 1 to about 2 molar equivalents of acid acceptor should be employed per mole of carbamate. Preferably an equimolar amount or slight molar excess of acid acceptor is utilized, for example about 1.0 to 1.75 molar equivalents of acid acceptor per mole of carbamate, preferably 1.0 to about 1.5. If a tertiary amine is used as the acid acceptor and complexing agent, sufficient amine must be present to take up or neutralize the hydrogen halide formed and to form a catalytic amount of the sulfur dioxide/alkylamine complex described above.

The reaction between the sulfenyl halide and the carbamate is suitably run at room temperature, but this temperature may vary, for example between 0° C. and 50° C.

The preferred embodiment of the invention is one in which a disubstituted aminosulfenyl chloride is prepared in accordance with reaction B to form a reaction mixture containing sulfur dioxide.

The equation for the reaction is as follows:

$(R^7R^8NS)_2 + ClSO_2Cl \rightarrow 2R^7R^8NSCl + SO_2$

The sulfur dioxide is formed in situ and remains in solution due to its solubility in the sulfenyl chloride. The solvent for the reaction is one in which the sulfenyl chloride is soluble, for example hexane or dimethylformamide (DMF) for the preparation of a di(lower)alkylaminosulfenyl chloride, or methylene chloride for the preparation of 4-morpholinylsulfenyl chloride. The reaction product containing the sulfenyl halide and $SO_2$ is then combined with sufficient triethylamine (TEA) to form a 1:1 complex with the sulfur dioxide (TEA.$SO_2$), an appropriate carbamate, and sufficient acid acceptor to remove the by-product hydrogen chloride. This procedure permits the preparation of the sulfenyl halide and the reaction of the sulfenyl halide with the carbamate to be performed in successive steps in a single reactor without isolation of intermediates. Thus the best mode for conducting the reaction is to form the sulfenyl chloride and $SO_2$ in situ and to add to the resulting reaction mixture appropriate amounts of the carbamate then triethylamine, the triethylamine acting as agent for the complexing of sulfur dioxide and also as an acid acceptor.

It is also possible, as shown in the examples, to prepare the disulfide starting material in situ in accordance with Reaction C.

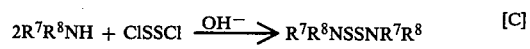

$2R^7R^8NH + ClSSCl \xrightarrow{OH^-} R^7R^8NSSNR^7R^8$     [C]

Thus all three steps may be conducted in a single solvent in a single reactor without isolation of intermediates.

The use of a catalytic amount of a complex of sulfur dioxide and a trialkylamine, is applicable to the sulfenylation of a wide variety of carbamates of formula I.

In that formula, $R^1$ and $R^2$ may be any group which is relatively inert, that is, which will not react with the sulfenyl halide in preference to the hydrogen atom on the carbamate nitrogen.

Typical carbamates suitable for use in the claimed process include, but are not necessarily limited to, compounds of formula I having the substitution patterns described below, bearing in mind that the critical parameter is that the substituents in $R^1$ and $R^2$ are relatively inert to reaction with the sulfenyl halide as indicated above.

In accordance with the foregoing, $R^2$ may be an alkyl group, advantageously an alkyl group of 1 to 10 carbon atoms, straight or branched chain, preferably lower alkyl of 1 to 4, most preferably 1 to 2 carbons. For example, $R^2$ may be methyl, ethyl, propyl, butyl, pentyl, hexyl, octyl, etc., preferably methyl, ethyl, propyl, or butyl, most preferably methyl or ethyl.

$R^1$ represents an inert organic carbamate residue and may be a wide variety of groups. Thus, $R^1$ may be, for example, (1) an alkyl group of 1 to 10 carbon atoms such as methyl, ethyl, propyl, i-propyl, butyl, hexyl, or octyl; advantageously alkyl of 1 to 6 carbon atoms, preferably a lower alkyl group of 1 to 4 carbon atoms; (2) a cycloalkyl group of 3 to 8 carbon atoms, advantageously 3 to 6 carbon atoms for example cyclopropyl, cyclopentyl or cyclohexyl; (3) an aromatic hydrocarbon of 6 or 10 ring carbon atoms, optionally substituted with one or more (up to about 3) substituents independently selected from halogen, lower alkyl, lower alkoxy, lower alkylthio, dioxalanyl, cyano, nitro, trihalomethyl, and di(-lower)alkylamino; or (4) an indanyl group optionally substituted with nitro or cyano.

$R^1$ may also be (5) a heterocyclic group of the formula

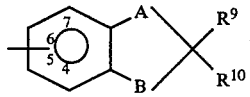

in which $R^9$ and $R^{10}$ are hydrogen, halogen, lower alkyl, or lower alkoxy, A and B are each oxygen or one of A and B is methylene optionally substituted with 1 or 2 lower alkyl groups, and the other of A and B is oxygen or sulfur, said heterocyclic group being attached at the 4, 5, or 7, preferably 4 or 7 position.

$R^1$ may also be (6) an imino group of the formula $R^{11}R^{12}C=N-$ in which $R^{11}$ and $R^{12}$ may be independently selected from a wide variety of substituents. For example, $R^{11}$ may be selected from hydrogen, halogen, alkyl of 1 to 8 carbon atoms, cyano, alkoxy of 1 to 4 carbon atoms, alkylthio of 1 to 4 carbon atoms, alkoxyalkyl of 2 to 4 carbon atoms, alkylcarbonyl of 2 to 4 carbon atoms, alkylthioalkyl of 2 to 4 carbon atoms, cyanoalkylthio of 2 to 4 carbon atoms, and phenyl optionally substituted with 1 to 3 groups selected from halogen, alkyl of 1 to 4 carbon atoms, alkoxy of 1 to 4 carbon atoms, and cyano; and $R^{12}$ may be selected, for example, from alkylthio of 1 to 8 carbon atoms, alkylcarbonyl of 2 to 10 carbon atoms, alkylthioalkyl of 2 to 8 carbon atoms, cyanoalkylthio of 2 to 6 carbon atoms, a phenyl group optionally substituted with 1 to 3 groups selected from halogen, lower alkyl, lower alkoxy, cyano, (lower)alkylaminocarbonyl, or phenyl; alkylsulfinyl of 1 to 8 carbon atoms, alkylsulfonyl of 1 to 8 carbon atoms, di-(alkylthio)alkyl, (phenyl)(lower alkylthio)-lower alkyl, phenylthio, phenylthioalkyl in which the alkyl group is 1 to 6 carbon atoms, phenylsulfonylalkyl in which the alkyl group is 1 to 4 carbon atoms, phenylmethylthioalkyl, phenylmethylsulfinylalkyl or phenylmethylsulfonylalkyl in which alkyl is 1 to 2 carbon atoms, amino or aminocarbonyl in which the nitrogen atom is substituted with two groups selected from formyl, lower alkanoyl or lower alkyl.

Alternatively $R^{11}$ and $R^{12}$ can be taken together with the carbon atom to which they are attached to form a 5 or 6 membered saturated ring which may contain as ring members 1 to 3 —O— groups, 1 to 3 —S— groups, 1 to 3

groups, 1 to 3

groups, one $NR^{13}$ group in which $R^{13}$ is lower alkyl, or which may contain an $NR^{13}$ group and an —O— or —S— group.

Table I illustrates a wide variety of carbamates wherein $R^1$ is an aromatic hydrocarbon, an indanyl group, a heterocyclic group or an imino group useful as substrates for sulfenylation. The preparation of such carbamates is well known to those skilled in the art.

A wide variety of sulfenyl halides of formula II may also be employed in the reaction. Representative sulfenyl halides of formula II include those in which X is a halogen atom such as chlorine, bromine or fluorine, preferably chlorine or bromine; $R^3$ may be a phenyl group optionally substituted with 1 to 3 substituents independently selected from groups such as halogen, lower alkyl, lower alkoxy, methylenedioxy, or cyano; a trihalomethyl group as in trichloromethylsulfenyl chloride. Illustrative substituted arylsulfenyl chlorides include those in which $R^3$ is 2,6-dichlorophenyl, 2,4,6-trichlorophenyl, 2-chloro-4-i-propylphenyl, 4-chloro-2,6-dimethylphenyl, 2-bromo-3-ethoxyphenyl, 2,6-dimethoxy-3-methylphenyl, 4-cyano-2-methylphenyl, 4-butyl-2,6-dimethylphenyl, and 2-chloro-4,5-methylenedioxyphenyl. $R^3$ may also be a disubstituted amino group of the formula $R^7R^8N-$ in which: (1) one of $R^7$ and $R^8$ is selected from an alkyl group of 1 to 10 carbon atoms, preferably a lower alkyl group, a cycloalkyl group of 3 to 6 carbon atoms, or a phenyl group optionally substituted with 1 to 3 substituents selected from halogen, lower alkyl, trihalomethyl, nitro, or benzyl; and the other of $R^7$ and $R^8$ is independently selected from an alkyl group of 1 to 10 carbon atoms, preferably a lower alkyl group; a cycloalkyl group of 3 to 6 carbon atoms; a phenyl group optionally substituted with 1 to 3 substituents selected, for example, from halogen or lower alkyl; a benzyl group; an $-SO_2R^{14}$ group in which $R^{14}$ is lower alkyl, benzyl, di(lower)-alkylamino, or phenyl optionally substituted with halogen, lower alkyl, nitro or trihalomethyl; (2) one of $R^7$ and $R^8$ is lower alkyl or phenyl and the other is $-COOR^{15}$ wherein $R^{15}$ is as defined for $R^1$ and is the same as or different from $R^1$; or (3) one of $R^7$ and $R^8$ is lower alkyl or phenyl and the other of $R^7$ and $R^8$ is a group of the formula

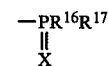

in which X is oxygen or sulfur, $R^{16}$ and $R^{17}$ are independently lower alkyl, lower alkoxy, lower alkylthio or $-NR^{18}R^{19}$ where $R^{18}$ and $R^{19}$ are independently lower alkyl, cycloalkyl of 3 to 6 carbon atoms or phenyl; or (4) $R^7$ and $R^8$ taken together with the nitrogen form a saturated heterocyclic ring of 5 to 8 members which may have an oxygen, sulfur, or $>N-CH_3$ linkage, optionally substituted on one or two carbon atoms with one or two lower alkyl groups.

Tables I and II illustrate a wide variety of sulfenyl chlorides, in addition to those mentioned above, useful in practicing the present invention.

The following examples will further illustrate the practice of the present invention.

EXAMPLE 1

This example illustrates preparation of 2,3-dihydro-2,2-dimethyl-7-benzofuranyl (dibutylaminothio)methylcarbamate in hexane by a three step procedure. Following the first step, the resulting bis(dibutylamino) disulfide is isolated. In the second step dibutylaminosulfenyl chloride and sulfur dioxide are produced in place. And in the third step the dibutylaminosulfenyl chloride is converted to the desired product in a reaction involving the in situ generation of the triethylamine/$SO_2$ complex.

A. Preparation of Bis(dibutylamino)disulfide

Dibutylamine (387.8 g, 3.0 moles) and recycled hexane (360 ml, containing 0.1% triethylamine) were charged to a five liter, jacketed reactor equipped with agitator. To this was added a solution of sodium hydroxide (144.9 g, 3.62 moles) in tap water (1092 ml). To this two-phase mixture, under nitrogen and stirred at 750 rpm, was added a solution of sulfur monochloride (232.5 g, 1.72 moles) in hexane (525 ml, containing 0.1% triethylamine) while iced water was circulated through the reactor jacket. The reaction temperature rose from 28° C. to 40° C. at which it was maintained by the exotherm. Addition time was 25 minutes. The mixture was agitated for an additional 20 minutes and then vacuum filtered. The two layers were allowed to separate giving an upper layer of disulfide solution (1078 g) and a lower aqueous layer. Two 25 ml samples of the disulfide solution were stripped to constant weight, giving an average crude bis(dibutylamino)disulfide concentration of 45% w/w, a weight yield of 100%, assaying an average 87% by hplc, balance bis(dibutylamino)polysulfides.

B. Preparation of Dibutylaminosulfenyl Chloride

The disulfide solution from Example 1A (789 g, 1.1 moles) was charged to a reactor, under nitrogen. Sulfuryl chloride (148.5 g, 1.1 mole) was added over a period of fifteen minutes at 20° C. with stirring. The product was a dark orange solution of dibutylaminosulfenyl chloride and sulfur dioxide in hexane.

C. Preparation 2,3-Dihydro-2,2-dimethyl-7-benzofuranyl (dibutylaminothio)methylcarbamate To the solution of sulfenyl chloride from Example 1B was added 460.8 g of 95% 2,3-dihydro-2,2-dimethyl-7-benzofuranyl methylcarbamate (2.0 moles). Triethylamine (354.2 g, 3.5 moles; containing 0.17% water) was added with stirring over a period of thirty-two minutes. The reaction temperature rose from 20° C. to 35° C. during the addition and was maintained at 35° C. by warm water in the jacket for a further 1.5 hours. The reaction mixture was cooled to 10° C. and tap water (880 ml) was added in five minutes to quench the reaction and dissolve the triethylamine salts. An exotherm occurred during the water addition, resulting in a final temperature of 20° C. The two layers were vacuum-filtered into a suction flask. The aqueous layer was separated and retained in order to recover the triethylamine. The organic layer was stripped on a rotary evaporator, finally at 50° C./133 Pa (1 mm), to give a dark brown oil of 2,3-dihydro-2,2-dimethyl-7-benzofuranyl (dibutylaminothio) methylcarbamate (792.8 g). Analysis by hplc showed a purity of 95%, indicating a chemical yield of 99%, based on starting carbamate.

The stripped hexane was retained for recycle.

EXAMPLE 2

This example illustrates preparation of 2,3-dihydro-2,2-dimethyl-7-benzofuranyl (dibutylaminothio)methylcarbamate in hexane in a single reactor in which all 3 steps are conducted without isolation of intermediates.

Over a period of 24 minutes a solution of sulfur monochloride (170.8 g., 1.27 mole) in 385 ml of hexane was added to a stirred mixture of dibutylamine (284.4 g, 2.2 mole) 263 ml of hexane, sodium hydroxide (106.3 g, 2.66 mole), and 801 ml of water. Addition rate was controlled to prevent the temperature from rising above 40° C. The mixture was stirred for an additional twenty minutes, and the aqueous layer was removed. The thermometer, stirrer blades, and reactor walls above the mixture were wiped to remove any moisture. Sulfuryl chloride (148.5 g, 1.1 moles) was added dropwise to the stirred mixture under nitrogen over a period of 19 minutes at a temperature of 20° C. 2,3-Dihydro-2,2-dimethyl-7-benzofuranyl methylcarbamate (98%, 451.4 g, 2.0 moles) was added to the mixture, followed by dropwise addition of triethylamine (354.2 g, 3.5 mole) over a period of 28 minutes. The mixture was stirred for two hours from the start of addition at 35° C. At the end of this time the mixture was cooled to 10° C. and 880 ml of water was added at a rate slow enough to keep the temperature at or below 20° C. The mixture was stirred for five minutes, then vacuum-filtered. The layers were separated and the organic layer was concentrated to provide 763.6 g of 93% (by hplc) 2,3-dihydro-2,2-dimethyl-7-benzofuranyl (dibutylaminothio)methylcarbamate (93% chemical yield based on the starting carbamate). During the filtration 15.88 g of unreacted 2,3-dihydro-2,2-dimethyl-7-benzofuranyl methylcarbamate and tars was recovered.

EXAMPLE 3

This example illustrates preparation of triethylamine/sulfur dioxide complex in hexane.

Sulfur dioxide (20 g, 0.312 mole) was bubbled into a solution of triethylamine (20 g, 0.198 mole) in 100 ml of hexane. Addition was stopped when the temperature began to drop. The mixture was stirred for fifteen minutes, and was concentrated in vacuo at 0° C. in an ice bath to yield 29.04 g of yellow liquid (88.8% yield as TEA.SO$_2$). The nmr and ir were consistent with a 1:1 molecular complex of triethylamine and sulfur dioxide.

EXAMPLE 4

This example illustrates the reaction of dibutylaminosulfenyl chloride and 2,3-dihydro-2,2-dimethyl-7-benzofuranyl methylcarbamate in hexane using triethylamine as acid acceptor and separately prepared triethylamine/sulfur dioxide complex as catalyst.

A flask was charged with 30.2 g of a 50% solution of dibutylaminosulfenyl chloride (0.077 mole) in hexane and 15.8 g of 98% 2,3-dihydro-2,2-dimethyl-7-benzofuranyl methylcarbamate (0.07 mole) was added. Triethylamine (7.8 g, 0.077 mole) was added to the mixture with agitation over a period of seven minutes. A temperature rise from 24.5° to 26° C. was observed. A portion (1.9 g, 0.0115 mole) of the triethylamine/sulfur dioxide catalyst prepared in Example 3 was added dropwise. The temperature gradually rose to 30° C., and was raised further by external heating to 35° C. for a total reaction time of 100 minutes from the beginning of triethylamine addition. Twenty minutes later the mixture was cooled to 11° C. and 31 ml of water was added and mixed. The mixture was filtered to remove a small amount of solid, separated, and the organic layer was concentrated to yield 26.64 g of 90% (hplc) 2,3-dihydro-2,2-dimethyl-7-benzofuranyl (dibutylaminothio)methylcarbamate (a 90% chemical yield based on the starting carbamate).

EXAMPLE 5

This example illustrates preparation of 2,3-dihydro-2,2-dimethyl-7-benzofuranyl (dibutylaminothio)methylcarbamate in hexane using pyridine as acid acceptor and separately prepared triethylamine/sulfur dioxide complex as catalyst.

A flask was charged with 15.8 g of 98% 2,3-dihydro-2,2-dimethyl-7-benzofuranyl methylcarbamate (0.07 mole) and 30.2 g of a 50% solution of dibutylaminosulfenyl chloride (0.077 mole) in hexane under nitrogen atmosphere. To this was added with stirring 7.5 g (0.0455 mole) of triethylamine/sulfur dioxide complex prepared as described in Example 3. Pyridine (6.1 g, 0.077 mole) was then added dropwise with stirring over a period of 16 minutes. The temperature increased from 20.5° C. to 23.5° C. Stirring was continued for three hours after the beginning of pyridine addition during which external heating was supplied to maintain a temperature of 35° C. The mixture was cooled to 10.5° C. and 31 ml of water was added. The mixture was filtered, separated, and the organic layer was concentrated to yield 18.99 g of 75% (by hplc) 2,3-dihydro-2,2-dimethyl-7-benzofuranyl (dibutylaminothio)methylcarbamate (53% chemical yield based on the starting carbamate).

EXAMPLE 6

This example illustrates preparation of methyl N-[[[(dipropylaminothio)methylamino]carbonyl]oxy]ethanimidothioate.

Sulfuryl chloride (1.48 g, 0.011 mole) was added dropwise to 8.6 g of a 33.8% solution of bis(dipropylamino)disulfide (0.011 mole) in hexane over a period of about 1–2 minutes at room temperature. The mixture was stirred for fifteen minutes. Methyl N-(methylcarbamoyloxy)ethanimidothioate (3.24 g, 0.02 mole) was added to the mixture followed by addition of triethylamine (3.54 g, 0.035 mole) over a period of eight minutes. The temperature rose from 20° C. to 35° C. and was then maintained at 35° C. with heating. The mixture was stirred for two hours after the start of triethylamine addition, during which time 10 ml of hexane was added to make stirring easier. At the end of the two hour period 15 ml of water was added and stirring was continued for five minutes. When the mixture was placed in a separatory funnel three layers appeared. Additional hexane (20 ml) caused the two upper layers to combine. The aqueous layer was separated and the organic layer was concentrated to give 5.90 g (100% weight yield) of methyl N-[[[(dipropylaminothio)methylamino]carbonyl]oxy]ethanimidothioate. The nmr spectrum was consistent with the expected product.

EXAMPLE 7

This example illustrates preparation of 1-naphthyl (dibutylaminothio)methylcarbamate.

Sulfuryl chloride (1.5 g, 0.011 mole) was added dropwise to 7.9 g of a 44.9% solution of bis(dibutylamino)disulfide (0.011 mole) in hexane while maintaining a temperature of 20° C. The mixture was stirred for fifteen minutes after the end of addition. 1-Naphthyl methylcarbamate (4.0 g, 0.020 mole) was added followed by dropwise addition of triethylamine (3.54 g, 0.035 mole) over a period of three minutes with stirring, during which time the temperature increased from 21° C. to 30° C. The temperature was increased by heating to 44° C. for two hours. The mixture was cooled to 11° C. and 15 ml of water was added. The aqueous layer was separated and the organic layer was concentrated to give 7.22 g of 94% (by hplc) 1-naphthyl (dibutylaminothio)methylcarbamate.

EXAMPLE 8

This example illustrates preparation of 2,3-dihydro-2,2-dimethyl-7-benzofuranyl (dibutylaminothio)methylcarbamate using triethylamine and gaseous sulfur dioxide in hexane.

Sulfur dioxide was passed through 30.2 g of a 50% solution of dibutylaminosulfenyl chloride (0.077 mole) in hexane until the solution had gained 2.8 g (0.044 mole). 2,3-Dihydro-2,2-dimethyl-7-benzofuranyl methylcarbamate (98%, 15.5 g, 0.069 mole) was added followed by dropwise addition of triethylamine (12.4 g, 0.123 mole) over a period of 28 minutes with stirring. Stirring was continued for about 18 hours. The mixture was cooled to 9.5° C., 31 ml of water and 40 ml of hexane were added, and the layers were separated. The organic layer was concentrated to yield 27.4 g of 94% (by hplc) 2,3-dihydro-2,2-dimethyl-7-benzofuranyl (dibutylaminothio)methylcarbamate (98% chemical yield).

EXAMPLE 9

This example illustrates preparation of 2,3-dihydro-2,2-dimethyl-7-benzofuranyl (4-morpholinylthio)methylcarbamate in methylene chloride.

Bis(4-morpholinyl)disulfide (11.8 g, 0.05 mole) was dissolved in 50 ml of methylene chloride and 7.3 g (0.10 mole) of dimethylformamide. The solution was cooled to 0° C. and sulfuryl chloride (6.75 g, 0.05 mole) was added in 5 minutes. To this mixture was added 2,3-dihydro-2,2-dimethyl-7-benzofuranyl methylcarbamate (22.1 g, 0.10 mole) and 50 ml of methylene chloride. Triethylamine (10.1 g, 0.10 mole) was added in 12 minutes. The mixture was stirred for 18 hours at room temperature and poured into 350 ml of ice water. The layers were separated and the organic layer was washed three times with 300 ml portions of brine, stirred with 1.5 g of 70–230 mesh silica gel for 20 minutes, filtered, and concentrated to give 33.9 g of 2,3-dihydro-2,2-dimethyl-7-benzofuranyl (4-morpholinylthio)methylcarbamate. The product contained 6.5% starting material by hplc. It was recrystallized from cyclohexane to give 27.0 g of white crystals (80% yield).

EXAMPLE 10

This example illustrates the reaction of carbofuran and dibutylaminosulfenyl chloride in hexane in the presence of triethylamine in the absence of sulfur dioxide.

A solution of dibutylaminosulfenyl chloride, prepared as in Example 1.A and B. was stripped of solvent and sulfur dioxide in a rotary evaporator to provide 64.5 g of residual dibutylaminosulfenyl chloride. Fresh hexane (100 ml) was added, and the sulfenyl chloride/hexane mixture was added to 68.4 g (0.3 mole) 2,3-dihydro-2,2-dimethyl-7-benzofuranyl methylcarbamate. Triethylamine (53.1 g, 0.525 mole) was added with stirring over a period of 30 minutes. The reaction temperature rose to 24° C. and was then heated to and maintained at 35° C. for 1.5 hours after addition of triethylamine was completed. The reaction mixture was then cooled to 10° C. then quenched over a period of 2 minutes with 132 ml of water. During water addition an exotherm occurred, resulting in a final temperature of 48° C. The resulting solution was stirred for an additional twenty minutes, vacuum filtered and the phases separated. Hplc analysis showed a purity of 4.5%, indicating a chemical yield of only 2.4% of 2,3-dihydro-2,2-dimethyl-7-benzofuranyl(dibutylaminothio)methylcarbamate.

It will be understood that the foregoing is merely illustrative and that the present invention may be practiced by conducting the reaction of an alkylcarbamate and sulfenyl halide in the presence of the trialkylamine/sulfur dioxide complex, without regard to the particular reactants selected. Thus, it will be apparent to those skilled in the art that many other sulfenyl halide/carbamate combinations can be selected in accordance with the foregoing teaching without departing from the spirit and scope of this invention.

TABLE I

| $R^1OOCNHR^2$ or $R^{15}OOCN{\diagdown}{{R^7}\atop{SCl}}$ | |
|---|---|
| $R^1, R^{15}$ | $R^2, R^7$ |
|  | $CH_3$ |

TABLE I-continued

| | |
|---|---|
| 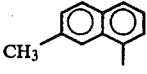 | CH₃ |
| 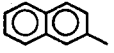 | CH₃ |
| 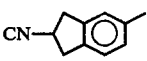 | CH₃ |
| 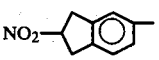 | CH₃ |
| 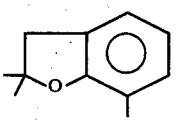 | CH₃ |
| 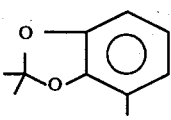 | CH₃ |
| 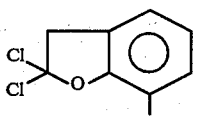 | CH₃ |
| 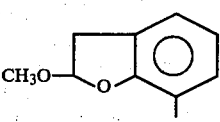 | CH₃ |
| 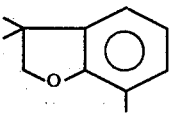 | CH₃ |
| 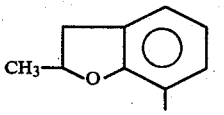 | CH₃ |

$R^1OOCNHR^2$ or $R^{15}OOCN\begin{smallmatrix}R^7\\SCl\end{smallmatrix}$ $R^1, R^{15} =$ 

| A | B | C | $R^2, R^7$ |
|---|---|---|---|
| H | H | H | CH₃ |
| 2-Cl | H | H | CH₃ |
| 2-CH₃ | H | H | CH₃ |
| 2-CH₃ | 4-CH₃ | H | CH₃ |
| 2-CH₃ | 4-CH₃ | 6-CH₃ | CH₃ |
| 2-CH(CH₃)₂ | H | H | CH₃ |
| 2-CH₃ | 6-CH(CH₃)₂ | H | CH₃ |
| 4-C(C₂H₅)₂ | H | H | CH₃ |
| 2-C(CH₃)₃ | 4-C(CH₃)₃ | H | CH₃ |
| 3-CH₂CH(CH₃)₂ | H | H | CH₃ |
| 2-Br | 4-OCH₃ | 6-Br | CH₃ |
| 2-OC₅H₁₁ | H | H | CH₃ |
| 2-CH₃ | 4-OC₂H₅ | 6-Br | CH₃ |
| 2-CH₃ | 4-SCH₃ | H | CH₃ |
| 2-SC₃H₇ | 4-Cl | H | CH₃ |
| 3-CH₃ | 4-SCH₃ | 5-CH₃ | CH₃ |
| 2-CH₂SC₂H₅ | H | H | CH₃ |
| 2-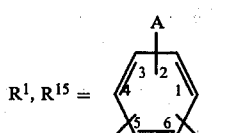 | H | H | CH₃ |
| 3-CH₃ | 4-N(CH₃)₂ | 5-CH₃ | CH₃ |
| 3-CH₃ | 4-N(CH₃)₂ | H | CH₃ |
| 2-Cl | 4-N(CH₃)(C₃H₇) | H | CH₃ |
| 2-CH₃ | 4-CN | H | CH₃ |
| 2-OCH(CH₃)₂ | H | H | CH₃ |
| 2-CCl₃ | H | H | CH₃ |

$R^1OOCNHR^2$ or $R^{15}OOCN\begin{smallmatrix}R^7\\SCl\end{smallmatrix}$ $R^1, R^{15} = R^{11}R^{12}C=N-$

| $R^{11}$ | $R^{12}$ | $R^2, R^7$ |
|---|---|---|
| H | –φ-C(O)N(CH₃)₂ | CH₃ |
| H | —C(C₃H₇)(SO)(C₂H₅) | CH₃ |
| H | —C(SC₃H₇)₂(CH₃) | CH₃ |
| H | —C(C₂H₅)(SCH₃)(φ) | CH₃ |
| H | —C(O)(CH₃) | CH₃ |
| H | —C(CH₃)₂(SCH₃) | CH₃ |
| H | φ | C₂H₅ |
| Cl | —CH₂SC₅H₁₁ | CH₃ |
| Cl | —C(O)(C₂H₅) | CH(CH₃)₂ |
| Cl | —CH₂SCH₂φ | φ |
| F | —CH₂SO₂CH₂φ | φ |
| Br | —(CH₂)₃SO₂φ | φ |
| CH₃ | —SC₂H₅ | CH₃ |
| CH(CH₃)₂ | —CH₂SCH₃ | CH₃ |
| C₂H₅ | 2-CNφ— | CH₃ |

TABLE I-continued

| | | |
|---|---|---|
| CH₃ | 2-Cl, 4CH₃φ | CH₃ |
| C₃H₇ | —S(CH₂)₄CN | CH₃ |
| CH₃ | 4-φ-2-Clφ- | CH₃ |
| C₂H₅ | —(CH₂)₅SC₂H₅ | C₂H₅ |
| CH₃ | —SO₂C(CH₃)₃ | C₃H₇ |
| CH₃ | —C(O)C(CH₃)₃ | C₂H₅ |
| C₅H₁₁ | —SC₅H₁₁ | C₇H₁₅ |
| C₈H₁₇ | —SOC₇H₁₅ | C₅H₁₁ |
| CH₃ | φ | CH₃ |
| C₂H₅ | —SOCH₃ | C₂H₅ |
| C₃H₇ | —SC₈H₁₇ | C₄H₉ |
| CH₃ | —SC₆H₁₃ | C₆H₁₃ |
| CH₂(CH₃)₂ | —SOC₄H₉ | C₈H₁₇ |
| C₂H₅ | —CH(CH₃)(SCH₃) | CH₃ |
| —CN | φ | CH₃ |
| —CN | —CON(CH₃)₂ | C₂H₅ |
| —CN | —N(COCH₃)(C₂H₅) | C₃H₇ |
| —CN | —COCH₃ | C₃H₇ |
| CN | —(CH₂)₂SCH₃ | C₄H₉ |
| —CN | —(CH₂)₂SOCH₂φ | CH₃ |
| —OC₂H₅ | —N(CHO)(C₂H₅) | CH₃ |
| —OC₃H₇ | —COC₃H₇ | C₃H₇ |
| —OC₂H₅ | —(CH₂)₄Sφ | CH₃ |
| —SCH₃ | —SCH(CH₃)₂ | CH₃ |
| —SCH₃ | —(CH₂)₂SCH₃ | C₂H₅ |
| —SCH₃ | —(CH₂)₄SO₂φ | CH₃ |
| —SC(CH₃)₃ | —CH₂SCH₃ | CH₃ |
| —SCH(CH₃)₂ | —COC₈H₁₇ | C₈H₁₇ |
| —CH₂OCH₃ | —SCH(CH₃)₂ | CH₃ |
| —CH₂OCH₃ | —SCH₃ | CH₃ |
| —COC₃H₇ | φ | C₄H₉ |
| —COCH₃ | —COCH₃ | C₂H₅ |
| —COC₂H₅ | —CH₂SCH₃ | CH₃ |
| —CH₂SCH₃ | —CH₂Sφ | CH₃ |
| SCH₂CN | —Sφ | CH₃ |
| φ | φ | CH₃ |
| φ | —SCH₃ | C₃H₇ |
| φ | —C(CH₃)₂SCH₃ | C₄H₉ |
| 2-Clφ | 2-Clφ | CH₃ |
| 4-C₄H₉φ | 2-CH₃Oφ | CH₃ |
| 2—CH₃-4-C₂H₅-6-CNφ | —SC₅H₁₁ | CH₃ |
| 2-Cl-4-C₂H₅-6-CNφ | —SC₅H₁₁ | CH₃ |
| 4-C₄H₉Oφ | —SCH₂CN | CH₃ |
| 2-CH₃-4-CH₃φ | —Sφ | CH₃ |

R¹OOCNHR² or R¹⁵OOCN$^{R7}_{SCl}$

R¹, R¹⁵ = 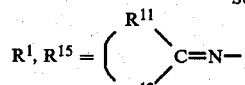

| R¹¹ + R¹² | R², R⁷ |
|---|---|
| 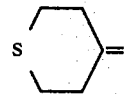 | CH₃ |

TABLE I-continued

| | |
|---|---|
| (oxane) | CH₃ |
| (N-methyl morpholine) | CH₃ |
| (1,3-dithiane) | CH₃ |
| (thiane S-oxide) | CH₃ |
| (thiane S,S-dioxide) | CH₃ |
| (1,3-dioxolane) | CH₃ |
| (1,3-dioxane) | CH₃ |
| (N-ethyl morpholine) | CH₃ |
| (trisulfone) | CH₃ |
| (trisulfoxide) | CH₃ |
| (1,3-dioxolane) | CH₃ |
| (N-methyl thiomorpholine) | CH₃ |

TABLE II

$R^7R^8NSCl$

| $R^7$ | $R^8$ |
|---|---|
| —CH$_3$ | —C$_2$H$_5$ |
| —CH(CH$_3$)$_2$ | —CH(CH$_3$)$_2$ |
| —C$_2$H$_5$ | —CH(CH$_3$)$_2$ |
| —CH$_3$ | —CH⌐CH$_2$ CH$_2$⌐ |
| —CH(CH$_3$)$_2$ | —CH⌐(CH$_2$)$_3$ CH$_2$⌐ |
| —CH$_3$ | —CH⌐(CH$_2$)$_4$ CH$_2$⌐ |
| —CH$_3$ | 2-Cl—4-CH$_3$φ— |
| —φ | 2,4-diCH$_3$φ— |
| 2,4-diClφ— | —CH$_2$φ |
| —CH(CH$_3$)$_2$ | 2-C$_2$H$_5$φ— |
| 2-CH$_3$—4-Clφ— | 2,6-diClφ |
| —CH$_2$φ | —CH$_2$φ |

$R^7R^8NSCl$  $R^8=SO_2R^{14}$

| $R^7$ | $R^{14}$ |
|---|---|
| CH$_3$ | 4-CH$_3$φ— |
| C(CH$_3$)$_3$ | 4-CH$_3$φ— |
| 4-Clφ— | 4-CH$_3$φ— |
| φ— | 4-CH$_3$φ— |
| 2,4-diClφ— | 4-CH$_3$φ— |
| —CH$_2$φ | 4-CH$_3$φ— |
| —CH$_3$ | —CH$_3$ |
| —CH(CH$_3$)$_2$ | —CH$_3$ |
| —CH$_2$ | —CH$_3$ |
| —φ | —CH$_3$ |
| —CH⌐(CH$_2$)$_4$ CH$_2$⌐ | —CH$_3$ |
| —CH(CH$_3$)$_2$ | 4-Clφ— |
| —CH(CH$_3$)$_2$ | φ— |
| —CH(CH$_3$)$_2$ | —CH$_2$φ |
| 4-CF$_3$φ— | 4-CF$_3$φ— |
| 2-NO$_2$φ— | 2-CCl$_3$φ— |
| —C$_2$H$_5$ | 2-NO$_2$φ— |
| —CH$_3$ | 2-CH$_3$φ— |
| —CH$_3$ | —N(C$_3$H$_7$)[CH(CH$_3$)$_2$] |
| —CH$_3$ | —N(CH$_3$)(C$_3$H$_7$) |
| —C$_2$H$_5$ | —N(CH$_3$)$_2$ |
| 2-CCl$_3$φ— | —N[CH(CH$_3$)$_2$] [CH$_3$] |
| —CH⌐CH$_2$ CH$_2$⌐ | 2-NO$_2$φ— |
| —CH$_3$ | 2-CH$_3$φ— |
| —C$_3$H$_7$ | 4-CH$_3$φ— |

$R^7R^8NSCl$ $R^8 = \underset{\underset{X}{\|}}{P}R^{16}R^{17}$

| $R^7$ | X | $R^{16}$ | $R^{17}$ |
|---|---|---|---|
| —CH$_3$ | O | —CH(CH$_3$)$_2$ | —OCH$_2$CH$_3$ |
| —φ | O | —CH$_3$ | —CH$_3$ |
| —CH$_3$ | O | —SCH$_3$ | —OC$_3$H$_7$ |
| —φ | S | —OCH$_2$CH(CH$_3$)$_2$ | —OCH$_2$CH(CH$_3$)$_2$ |
| —CH$_3$ | S | —SCH$_3$ | —SC$_2$H$_5$ |
| —CH$_3$ | S | —CH$_3$ | —OC$_2$H$_5$ |
| —CH$_3$ | S | —C$_2$H$_5$ | —C$_2$H$_5$ |
| —φ | O | —OC$_2$H$_5$ | —N(CH$_3$)$_2$ |
| —CH$_3$ | O | —SCH$_3$ | —N(CH$_3$)(φ) |
| —CH$_3$ | S | —N(CH$_3$)$_2$ | —N(CH$_3$) (CH⌐CH$_2$ CH$_2$⌐) |

TABLE II-continued

| | | | |
|---|---|---|---|
| —φ | S | —N(CH₃)(φ) | —N(CH₃)(φ) |
| —φ | O | —OC₂H₅ | —N(φ)₂ |
| —φ | O | —Oφ | —N(φ)(CH—CH₂—CH₂) |
| —φ | O | —SCH₃ | —N(CH₃)₂ |
| —CH₃ | O | —S—CH₂—CH₂—CH₂ | —N(φ)(CH—CH₂—CH₂) |
| —C₂H₅ | O | —O—CH—(CH₂)₄—CH₂ | —N[C(CH₃)₃][CH(CH₃)₂] |
| —C₃H₇ | O | —SC₂H₅ | —N(C₄H₉)(—CH—(CH₂)₄—CH₂) |
| —C₄H₉ | O | —N(CH₃)(—CH—CH₂—CH₂) | —N(CH₃)(—CH—(CH₂)₄—CH₂) |
| —CH₃ | O | —N(CH₃)₂ | —N(φ)(—CH—CH₂—CH₂) |
| —φ | O | —N(φ)(CH—(CH₂)₄—CH₂) | —N(φ)(C₂H₅) |
| —φ | S | —OCH₃ | —N(C₂H₅)(CH₃) |
| —φ | S | —SC₂H₅ | —N(C₂H₅)(—CH—(CH₂)₃—CH₂) |
| —φ | S | —N(CH₃)(CHCH₂CH₂) | —N(φ)(CHCH₂CH₂) |
| —CH₃ | S | —Oφ | —N(φ)(C₄H₉) |
| —C₂H₅ | S | —SCH₃ | —N(φ)(CH₃) |
| C₃H₇ | S | —NHC₂H₅ | —N(CHCH₂CH₂)(CH(CH₂)₄CH₂) |
| —C₄H₉ | S | —CH₃ | —N(φ)₂ |
| —CH₃ | S | φ | —N(C₄H₉)(CH₃) |
| —C₂H₅ | S | —CHCH₂CH₂ | —N(CH₃)(CHCH₂CH₂) |

| R⁷ + R⁸ | R⁷ + R⁸ |
|---|---|
|  | 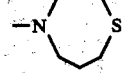 |
| 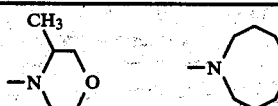 | 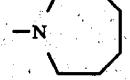 |
| 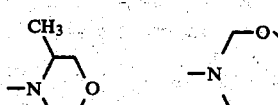 | 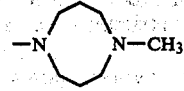 |

TABLE II-continued

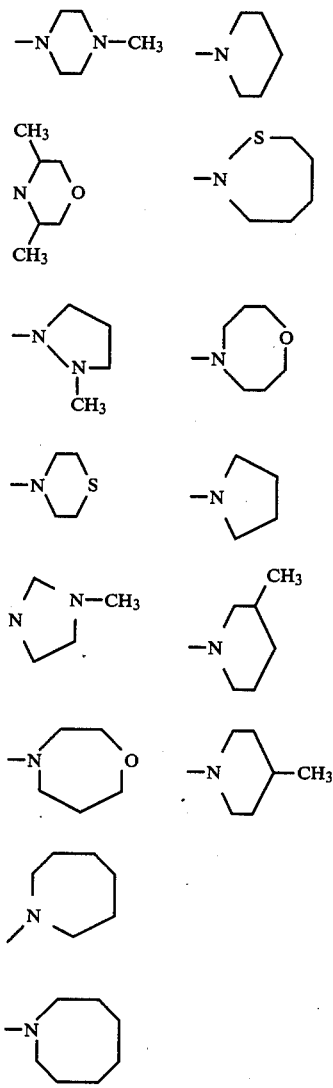

We claim:

1. In a process for sulfenylating an N-alkyl carbamate with a sulfenyl halide in a solvent in the presence of an acid acceptor, the improvement which comprises reacting said N-alkylcarbamate and a sulfenyl halide in the presence of a catalytic amount of a complex of sulfur dioxide and a trialkylamine of the formula $R^4NR^5R^6$ wherein each of $R^4$, $R^5$, and $R^6$ is a lower alkyl group.

2. The process improvement of claim 1 in which each of $R^4$, $R^5$ and $R^6$ is an alkyl group of 1 to 2 carbon atoms.

3. The process improvement of claim 1 wherein the trialkylamine is triethylamine.

4. The process improvement of claim 1 wherein said complex comprises an equimolar amount of sulfur dioxide and triethylamine.

5. The process improvement of claim 1 wherein there is employed at least 0.01 moles of sulfur dioxide and triethylamine, or the complex thereof, per mole of carbamate, and wherein the sulfenyl halide is a sulfenyl chloride.

6. The process improvement of claim 1 comprising forming the sulfenyl halide and sulfur dioxide in situ by reacting together a bis(disubstituted amino) disulfide and sulfuryl chloride in a solvent for the resulting sulfenyl chloride, said solvent also being employed for reaction of the sulfenyl chloride with said N-alkyl carbamate.

7. The process improvement of claim 1, 2, 3, 4, 5 or 6 in which the solvent is selected from aromatic hydrocarbons of 6 to 10 carbon atoms, halogenated aliphatic hydrocarbons of 1 to 4 carbon atoms, aliphatic hydrocarbons of 5 to 10 carbon atoms, or dimethylformamide.

8. The process improvement of claim 7 in which the solvent is selected from an aromatic hydrocarbon of 6 to 10 carbon atoms or a saturated aliphatic hydrocarbon of 5 to 10 carbon atoms.

9. The process improvement of claim 8 in which the solvent is a saturated aliphatic hydrocarbon of 5 to 8 carbon atoms.

10. The process improvement of claims 1, 2, 3, 4, 5, or 6, wherein triethylamine or pyridine is employed as acid acceptor.

11. The process improvement of claim 10 wherein triethylamine is employed as acid acceptor.

12. The process improvement of claims 1, 2, 3, 4, 5, or 6, wherein said carbamate is a lower alkylcarbamate.

13. The process of claim 12 wherein said carbamate is carbofuran, said sulfenyl chloride is a compound of the formula $R^7R^8$—NSCl and the resulting aminosulfenyl carbamate is a compound of the formula

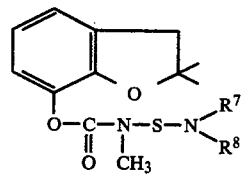

in which $R^7$ and $R^8$ are each alkyl groups of 1 to 10 carbon atoms.

14. The process improvement of claim 13 wherein $R^7$ and $R^8$ are each n-butyl groups.

UNITED STATES PATENT AND TRADEMARK OFFICE
CERTIFICATE OF CORRECTION

PATENT NO. : 4,329,293

DATED : May 11, 1982

INVENTOR(S) : John W. Ager; Maurice J.C. Harding; Charles E. Hatch, III

It is certified that error appears in the above—identified patent and that said Letters Patent is hereby corrected as shown below:

Column 2, line 48, "$R^3SSR^3 + ClSO_2Cl2R^3SX + SO_2$" should read --$R^3SSR^3 + ClSO_2Cl \quad 2R^3SX + SO_2$--. Column 12, line 47, "$-C(C_3H_7)(SO)(C_2H_5)$" should read -- $-C(C_3H_7)(S\emptyset)(C_2H_5)$--. Column 13, line 59, "$R^1OOCNHR^2$ or $R^{15}OOCN\begin{smallmatrix}R^7\\SCl\end{smallmatrix}$" should read --$R^1OOCNHR^2$ or $R^{15}OOCN\langle\begin{smallmatrix}R^7\\SCl\end{smallmatrix}$--.

Column 17, line 48,

"$\begin{smallmatrix}R^7\\R^8\end{smallmatrix}\rangle N\ SCl$"   should read   --$(\begin{smallmatrix}R^7\\R^8\end{smallmatrix}\rangle N\ SCl$--.

Signed and Sealed this

Twenty-third Day of April 1985

[SEAL]

Attest:

DONALD J. QUIGG

Attesting Officer

Acting Commissioner of Patents and Trademarks